(12) United States Patent
Katz

(10) Patent No.: US 6,326,022 B1
(45) Date of Patent: Dec. 4, 2001

(54) SLOW-RELEASE DISPOSABLE ELASTOMERIC BUCCAL DEVICES

(76) Inventor: Harry S. Katz, 785 Pleasant Valley Way, W. Orange, NJ (US) 07052

( * ) Notice: Subject to any disclaimer, the term of this patent is extended or adjusted under 35 U.S.C. 154(b) by 0 days.

(21) Appl. No.: 09/433,893

(22) Filed: Nov. 4, 1999

(51) Int. Cl.[7] .............................. A61K 9/10; A61M 37/00; A61P 25/34
(52) U.S. Cl. ........................ 424/435; 424/400; 514/953; D24/156
(58) Field of Search ..................................... 424/435, 484, 424/486, 400; D24/156; 533/105; 514/953

(56) References Cited

U.S. PATENT DOCUMENTS

| | | | |
|---|---|---|---|
| D. 264,125 | * | 4/1982 | Biggs . |
| D. 265,246 | * | 6/1982 | Jermyn . |
| D. 281,904 | * | 12/1985 | Linkow et al. . |
| D. 292,124 | * | 9/1987 | Roden et al. . |
| D. 399,562 | * | 10/1998 | Mendoza . |
| D. 428,653 | * | 7/2000 | Bergström et al. . |
| 3,754,332 | * | 8/1973 | Warren, Jr. . |
| 4,020,558 | * | 5/1977 | Cournut et al. . |
| 4,175,326 | * | 11/1979 | Goodson . |
| 4,764,377 | * | 8/1988 | Goodson . |
| 4,764,378 | * | 8/1988 | Keith et al. . |
| 4,861,268 | * | 8/1989 | Garay et al. . |
| 5,993,413 | * | 11/1999 | Aaltonen et al. . |
| 6,106,286 | * | 8/2000 | Gupta . |

* cited by examiner

*Primary Examiner*—Edward J. Webman

(57) ABSTRACT

Low-cost disposable elastomeric devices are conveniently insertable to grip between teeth and are easily removable. The devices contain substances such as odorants or medications which slowly permeate into the mouth. The preferred embodiment has a mushroom shaped head, containing the active substance, with a stem that engages between teeth to hold the device in place.

13 Claims, 3 Drawing Sheets

FIG.IA
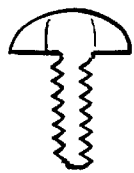
FIG.IB
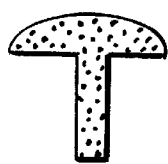
FIG.IC
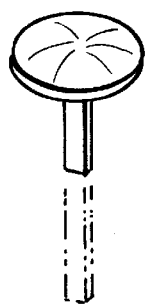
FIG.2
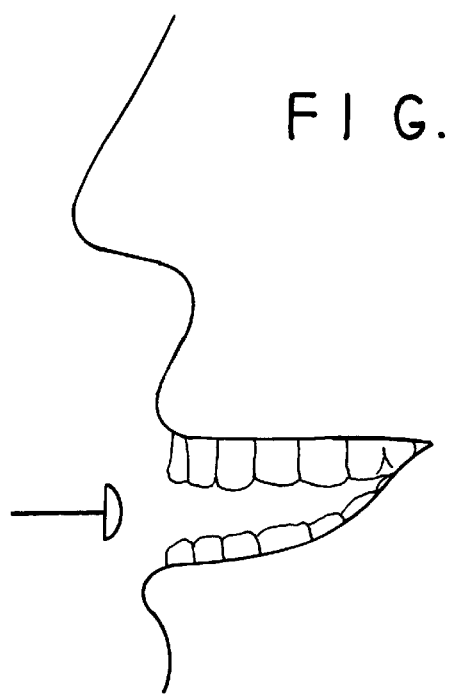
FIG.3
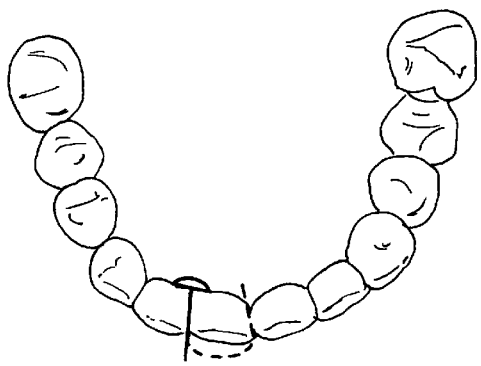
FIG.5
FIG.4
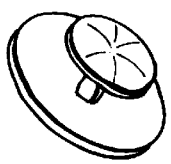
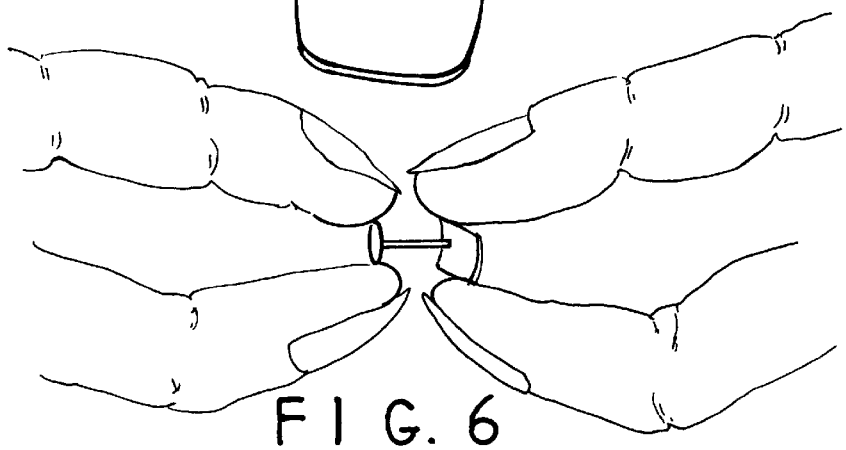
FIG.6

SLOW-RELEASE DISPOSABLE ELASTOMERIC BUCCAL DEVICES

REFERENCES CITED

U.S. PATENT DOCUMENTS

| | | | |
|---|---|---|---|
| 4,206,757 | 6/1980 | Grandadam et al | 128/260 |
| 4,627,852 | 12/1986 | von Bittera, et al | 604/897 |
| 5,205,820 | 4/1993 | Kreisel | 604/85 |
| 5,368,570 | 11/1994 | Thompson et al | 604/131 |
| 5,413,572; | 5/1995 | Wong et al | 604/891.1 |
| 5,419,771; | 5/1995 | Kreisel | 604/132 |
| 5,649,910; | 7/1997 | Kriesel et al | 604/133 |
| 5,656,032. | 8/1997 | Kriesel et al | 604/132 |

BACKGROUND OF THE INVENTION

1. Field of the Invention

This invention involves a disposable device, manufactured by use of a rubber or elastomer matrix, which contains an active ingredient that will slowly permeate out and into the mouth. The device is quickly and easily placed into the mouth, where it is held in a fixed position between two teeth in an unobtrusive manner, and can be quickly removed.

There is a need for devices that will provide slow and controlled release of functional materials or substances within the body of humans and animals. Simple and obvious examples of this need are the chewing gum products, which contain various substances such as peppermint or spearmint odorants to provide a pleasant breath, and medications such as nicotine additive as a means for helping to stop the smoking habit. There are also complex devices, as described below, that permit very precise slow release of drugs within the body. My invention fits into the wide gap between the very simple chewing gum and the complex drug delivery devices. My invention is a novel family of low cost disposable devices, which provide the slow release of substances within the mouth, as a convenient means to satisfy this need. My invention involves a novel combination of materials and designs.

2. Description of Prior Art

Prior art in this field discloses that there has been a great deal of industrial research that is directed toward the development of controlled release or slow release of substances or drugs within the body of humans and animals. Typical efforts in this field were printed in a recent publication of the American Chemical Society, Polymer Preprints of Papers presented at the Anaheim, Calif. Meeting in March 1999. A paper on page 253 was titled, FEASIBILTY ASSESSMENT AND RAPID DEVELOPMENT OF ORAL CONTROLLED RELEASE PROTOTYPES, by Avimesh G. Thombre, Pfizer Central Research. This paper's "focus is on the factors that should be considered in the feasibility assessment and strategies that can be employed to rapidly progress prototype oral controlled release dosage forms to clinical evaluation". This paper does not describe any device for controlled release of a drug. In the same publication, there is a paper, page 256, entitled, STRATEGIES OF ORAL DRUG DELIVERY, by Vincent H. L. Lee, University of Southern California. This paper states that, "The time is ripe for the development of innovative drug delivery systems. " The author discusses the interplay of polymer chemistry and cell biology as a means for the development of oral drug delivery systems, but does not mention any device that may be useful for this type of application. In the same publication, pages 322–323, there is a paper entitled, "SOLUBILITY CONSIDERATIONS AND DESIGN OF CONTROLLED RELEASE DOSAGE FORMS, by G. M. Venkatesh, SB Pharmaceuticals, Collegeville, Pa. This paper describes" four different approaches for developing controlled release dosage forms for bioactive materials . . . " The paper does not refer to any simple disposable device, such as my invention, that could be used for this type of application.

I anticipate that my invention of a relatively simple device for slow delivery of substances into the oral cavity will be a significant contribution to this field, even though my invention will not be suited for many stringent applications where very high precision in the rate of release is desirable or necessary.

An important point to repeat and emphasize is that prior art devices for the slow release of substances, have been either simple chewing gums/lozenges or complex and expensive devices, so that my invention is an innovative and nonobvious device for this type of application. My devices do not have the many drawbacks of chewing gums, which include an unfavorable user appearance due to factors such as the visible chewing action or the large bulge of gum that is usually apparent as a protruding spot along the lips. Also, the chewing action is tiresome for the user, and the loose gum within the mouth makes it awkward to speak in a normal manner or tone. Lozenges provide a relatively fast release of a substance and, during use, cause an interference with normal speech. My devices are secured in a stationary position within the mouth, and designed so that they are not obvious to observe and the user can become accustomed to its use so that speaking is not significantly hindered.

Pertinent patents related to slow release technology are the following U.S. Pat. Nos.:

4,206,757; 4,627,852; 5,205,820; 5,368,570; 5,413,572; 5,419,771; 5,649,910; and 5.656,032.

U.S. Pat. No. 4,206,757 is titled, DEVICE FOR THE ADMINISTRATION OF MEDICINAL SUBSTANCES, and involves a medical substance in a flexible cup, which is pressed against a subject's ear skin by a pin passing through the cup and ear. U.S. Pat. No. 4,627,852 is titled ACTIVE COMPOUND RELEASE SYSTEMS, and "relates to a system for the release of active compounds to the skin over a prolonged period, in particular to antiphlogistic medical plasters." U.S. Pat. No. 5,649,910 is titled FLUID DELIVERY APPARATUS AND METHOD OF MAKING SAME, and relates to a complex apparatus, which includes a visual flow indicator, for "infusing medical agents into an ambulatory patient at specific rates over extended periods of time." This cited patent will deliver fluids to a patient in precise quantities and "at extended microfusion rates overtime." U.S. Pat. Nos. 5,205,820; 5,368,570; 5,419,771 and 5,656,032 relate to apparatus and methods for accurately infusing fluid s into a patient at specific rates over an extended period of time.

SUMMARY OF THE INVENTION

A primary object of the present invention is to provide a simple low-cost device that will be functional and convenient, and will slowly release an active substance into the mouth. It is a further object of this invention to provide disposable units that are readily manufactured in large quantities. Another object is to provide a simple device for use in situations where there is no need for high precision in the rate of delivery of the substance.

BRIEF DESCRIPTION OF DRAWINGS

FIGS. 1A, 1B, 1C are side angled sketches of typical devices per my invention.

FIG. 2 shows a device per my invention being inserted in the oral cavity.

FIG. 3 shows the device being gripped and held between the teeth, due to the tendency of the stretched elastomer to return to its original thickness.

FIG. 4 is a side angled view of a device that has the appearance of two small round buttons connected by a thin elastomer material stem.

FIG. 5 is a side angle view of a device per this invention that has the appearance of a small round button connected to larger rectangular button by a thin elastomer rod or stem.

FIG. 6 shows the FIG. 5 device being stretched before insertion between teeth.

FIG. 16 shows the active substance containing disc.

FIG. 17 shows a device as in FIG. 1.

FIG. 18 shows the FIG. 16 disc slipped over the stem of the FIG. 17 device.

DESCRIPTION OF PREFERRED EMBODIMENTS

Figure 7:
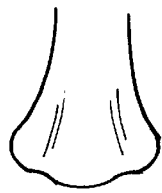
FIG. 7 shows the device in place between teeth.

My invention involves the use of rubber or elastomeric polymers that are filled or formulated with substances, which may be liquid or solid, that will permeate out when the molded device is within the mouth. In essence, the device may be considered as a combination of an active substance within a polymer matrix. The active substance may be a liquid odorant that will provide a pleasing breath odor for the wearer, or a drug that will provide a medical benefit. The active substance may also be a solid filler, which will be dissolved by the permeating saliva, and will then permeate into the mouth. Conditions within the oral cavity include exposure to saliva and a temperature of about 98.6 F. When my devices are exposed to the conditions within the oral cavity, the active substance will exude or permeate out at a rate that will be influenced by a number of factors. Among these factors are the shape of the device, the surface area to volume ratio of the device, the concentration of the active substance and permeation characteristics of the polymer matrix. There are many different rubbers and elastomer polymers that are non-toxic and can be used as the matrix. An example of polymers that have been used in the mouth are the acrylic polymers that are molded as dentures or composite tooth fillings and these have an established history of safe long term use. Other polymers have been used to manufacture athletic mouth-guards. Polymers that are preferred for my invention are rubbers or elastomers.

The American Society for Testing and Materials (ASTM), Philadelphia, Pa., has a Compilation of Standard Definitions in which film permeability is defined as "the measure of the rate at which chemical reagents penetrate a film". Permeation rate may be considered as the rate at which a liquid substance will penetrate or diffuse through a non-porous polymer. Polymers have different permeation rates that depend on the molecular structure of the polymer. This is often an important factor in the choice of a polymer film for specific applications, such as food packaging. Polyvinylidene chloride ( Dow Chemical's Saran) film usually has a much lower permeation rate than most packaging films and, therefore, is often selected for critical food packaging and food wrap applications where it is desirable to have substances such as water retained within the package.

Polyethylene tubes are often used for packaging toothpaste, but flavor ingredients can penetrate the tube wall at a relatively fast rate so that special "barrier coatings" are applied to the polyethylene tubes. The main point of this discussion is that the polymer matrix must be carefully selected in order to provide the optimum rate of diffusion of the active substance for each application of my devices. In some applications, silicone rubber will be the best matrix because active substances will permeate at a relatively high rate. There are many publications that present a good description of permeation factors for polymers and an example is the book titled, PERMEABILITY OF PLASTIC FILMS AND COATINGS, Edited by H. B. Hopfenberg and published by Plenum Press, New York, 1974. The information in this publication shows that there is a wide choice of polymers, and each provides characteristic permeation rates and other properties.

There are many different candidate non-toxic rubbers and elastomeric polymers that can be selected and tested for use in my slow release devices. Among the preferred choices are RTV silicone rubber, elastomeric thermoplastic olefins, flexible methacrylate polymers and co-polymers and ethylene vinyl acetate polymers.

The following is a partial list of some specific materials that have been molded as trial devices for my invention.

| Company | Trademark | Product No. |
| --- | --- | --- |
| Dow Corning Corporation | Sylgard RTV Silicone Rubber | 186 |
| Dynaflex | Kraton | D2122 |
| Dynaflex | Kraton | 7431-1 |
| Dynaflex | Kraton | 7820-1 |
| Dynaflex | Kraton | 7980-1 |

-continued

| Company | Trademark | Product No. |
|---|---|---|
| Dynaflex | Kraton | CL-40 |
| Advanced Elastomeric Systems | Vistaflex | 671N |

The following is a partial list of some of the odorants that have been used to make devices per my invention:

| Company | Trademark | Product No. |
|---|---|---|
| Virginia Dare | Lemon-Lime | RA54 |
| Virginia Dare | Peppermint Oil | HD30 |
| Virginia Dare | Fruit Gum | MN75 |
| Virginia Dare | Spearmint Oil | HF40 |
| Crompton & Knowles | Spearmint Oil | DP501527 |

As mentioned above, a convenient and good matrix for fabrication of my devices is Room Temperature Vulcanizing (RTV) silicone rubber. There are many grades of RTV, produced by companies that include Dow Corning Corporation and General Electric Co. When using this type of product, about 10% by weight of a liquid catalyst is mixed with the silicone rubber viscous polymer and the catalyzed mixture will then cure to a solid rubber within a relatively short period of time. The cure time, appropriate curing temperature and final hardness of the rubber can be predetermined and controlled as a result of experience with the selection and formulation of many ingredients for this family of rubber products. In the preparation of trial quantities of my devices, small batches of about 10 grams to 30 grams of Dow Corning's Sylgard 164 were mixed and placed into a plastic syringe. The mixture was then injected into a three cavity "mushroom" mold. For injection molding of large quantities, the mold cavities can be increased to any desirable size. The "mushroom" design is described later in this disclosure. The mold was then placed into an oven set at 180 F. for a period of time to convert the liquid mix to a rubbery solid. A higher temperature can be used to reduce the curing time. Alternatively, the mold was kept at room temperature for about 30 hours to convert the mix to a solid. After the cure cycle, the mold was opened to remove the rubber "mushrooms". Devices were made by either including the active substance in the mixture before molding, or by exposing the molded device to the active liquid ingredient in an enclosure so that the active ingredient permeated into the device. The final device was packaged in an aluminum foil laminate so that the active ingredient is contained upon long term storage prior to use. The end user opens the package and places the device in the mouth between two teeth as shown later in this disclosure.

I have noted that the addition of a fine particle size microporous filler, with interconnecting pores such as diatomaceous earth fillers, when added in concentrations of from 5 to 25% by weight to the polymer matrix, usually provide a matrix with improved capability to retain the active ingredient so that it exudes at a slower rate. However, my devices also perform satisfactorily without this type of additive.

A convenient laboratory machine for molding small thermoplastic parts is the Mini-Max Molder that is available from CSI, Cedar Knolls, N.J. This equipment permits molding or mixing and molding plastic materials or thermoplastic composites in batches as small as two to four grams. Thus, one batch is suitable for trial moldings that were made in a 3-cavity "mushroom" mold. In a typical trial run, about 3 grams of Elastomeric Systems's Vistanex polymer pellets were placed into the machine chamber, which had been heated to 185° C. After rotating the rotor for several minutes to obtain a uniform melt of the polymer, it was injected into the mold. The mold was then cooled to room temperature, and the molded mushrooms removed. As indicated above, there are many ways for including the active ingredient within the matrix polymer. A main procedure is to include the active ingredient within the molding compound. This is my preferred method when the base polymer in my device is an RTV silicone rubber as described in the preceding paragraph. When the device is manufactured by use of a thermoplastic elastomer, it is necessary that the polymer will be subjected to heat during the molding procedure. The heat may adversely effect the active ingredient or may volatilize it so that the concentration will be below the optimum level. Therefore, I have found it effective to treat molded thermoplastic devices with an active ingredient in liquid form, by placing them within an enclosure at room temperature or slightly elevated temperature for a period of time that will be adequate for a sufficient quantity of active ingredient to permeate into the device. The outer surface of the device is then wiped clean and packaged in an impermeable aluminum foil laminate container.

A typical preparation for a single device that was molded from RTV silicone rubber, was to place it onto aluminum foil, add two to three drops of the active ingredient, such as Virginia Dare Peppermint Oil HD30 or Spearmint Oil HF40 and then fold over the foil with double folds on each open edge. This closed container was allowed to remain overnight; the package was opened and excess liquid was quickly wiped off the device by use of a paper towel. The treated device was immediately repackaged in another sheet of aluminum foil. It was noted that the treated device could be stored in an enclosure of aluminum foil or foil laminate for weeks without loss of any significant amount of the active odorant. Indications are that the foil laminate packages will retain the activity of these devices for many years. When the package was opened and placed into the mouth, a pleasant odor of the active ingredient persisted on the user's breath for over 3 hours.

It was noted in trials with the thermoplastic elastomers mentioned above, that some of the active ingredients will result in a significant weakening of the tensile strength of the polymer, such that the stem will break when stretched beyond about 50% elongation. Also, that some polymers, such as Vistoflex 671N has the characteristic of retaining most of its elongation upon stretching, rather than returning to the original length that is the usual behavior of a true rubber. In spite of that characteristic, the Vistoflex polymer has generally better resistance to loss of strength upon exposure to the typical odorants that were used, and had sufficient tendency to increase in thickness after release of the stretching force, so that it proved to be a good matrix for this application. However, the results of many tests that involved permutations of polymer matrices and active ingredients makes it apparent that for each application there must be a judicious selection of matrix, form of active ingredient, processing method and packaging material.

The preferred elastomer matrices for my invention are the RTV silicone rubbers and thermoplastic elastomers that have FDA approval for dental and/or medical applications. Among the characteristics of these materials is the capability of being stretched to decrease the thickness and then relaxed to return partially or completely to the original shape or thickness. Thus my invented device is easily placed into position between two teeth and when the stretching tension is removed, the device stem will increase in thickness and be locked in place. Then the active ingredient will permeate slowly into the mouth. The active ingredient can be an odorant that will provide a pleasant smelling breath for the user, or nicotine or a nicotine simulant as a means for stopping the smoking habit, or a medication for various patient needs.

FIG. 1A shows a preferred configuration of my invention. The molded elastomeric polymer is shaped like a small mushroom, with a head and a small diameter or rectangular stem of the same elastomeric material. A preferred size for the head is about ⅜-inch in diameter and ⅛-inch thick at the apex, and the stem about 0.3-inch in length and 0.06-inch square or diameter. The weight of an RTV silicone rubber device that contains no active substance is about 0.16 grams. Moreover, a preferred variation involves a circular stem with outer protrusions or corrugations in a spiral configuration. This is conveniently provided by the use of a standard machinist's threading device through the hole of the mold that provides the stem molding. The outer protrusions provide an additional mechanical locking in place so the mushroom head is held tight against the back tooth surface since deep extension into the mouth could cause annoyance to the tongue and make speaking awkward.

FIG. 1B is a similar device with the inclusion of a porous filler such as diatomaceous earth in the elastomeric polymer.

FIG. 1C is a similar device with a rectangular cross section stem instead of the circular stem indicated in FIGS. 1A and 1B.

FIG. 2 shows the device about to be placed within the mouth.

FIG. 3 shows the device as it is gripped between two teeth. This can be accomplished by either a single short stem between the teeth or by use of a long stem molding wherein the stem can be looped between the adjacent teeth as shown in the sketch. Stretching during insertion thins the stem so that it can easily be inserted between the teeth. When the stretching force is removed, the stem will revert to a larger diameter or thickness and this provides the mechanism that causes the device to be firmly locked in the chosen position.

The wearer of my device has a number of obvious choices in the exact manner to be used. The device can be inserted between any two teeth with the usual small gap between teeth. Experiments have proven that a preferred location is between an upper central incisor tooth and the adjacent lateral incisor. Another common choice is between the upper lateral incisor and the canine tooth. Another choice relates to the wearer's tolerance for the slight protrussion of the thin soft stem against the inside of the lip. It has proven safe to use a small scissors to snip off the stem close to the outer surface of the tooth so that the remaining short stem does not exert any pressure upon the inside of the lip.

FIG. 4 shows another device per this invention wherein the device has two circular buttons connected with a short stem.

FIG. 5 shows a device wherein the device has a small circular button connected with a short stem to a larger rectangular button.

FIG. 6 shows the user stretching the device shown in FIG. 5 prior to placing it in position between two teeth.

FIG. 7 shows the FIG. 5 device placed between two teeth by the user. The smaller diameter button is preferably placed in front so that there is no very obvious indication that the wearer is using a device.

Figure 8:
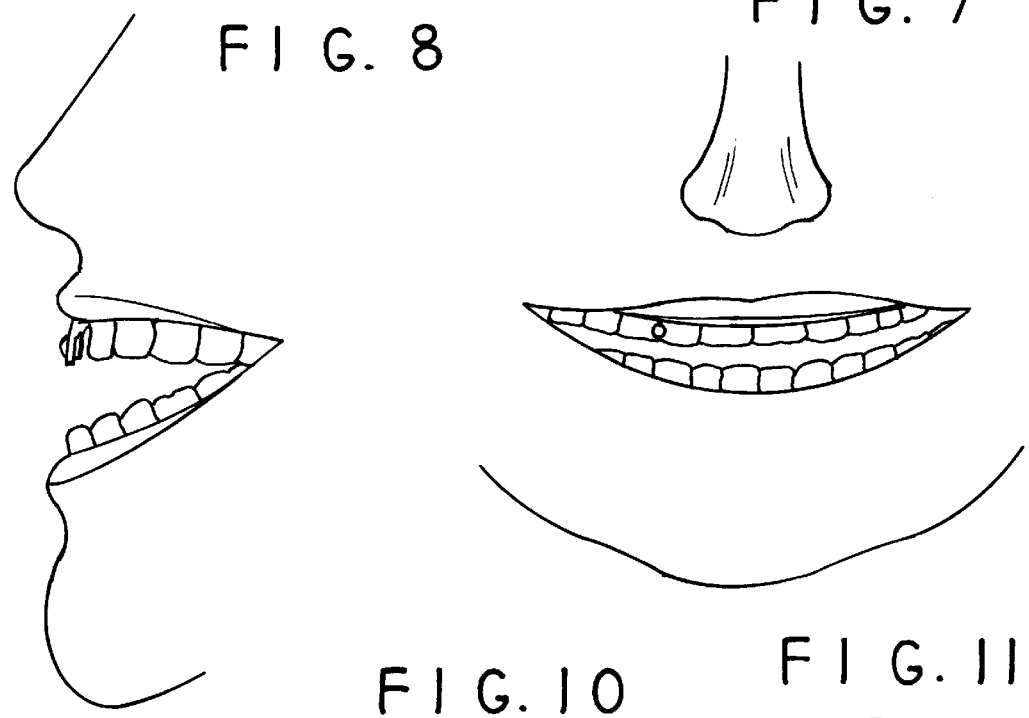
FIG. 8 is a side view showing the device in a wearer's mouth.

FIG. 8 is a side view showing the device in a wearer's mouth.

Figure 9:
FIG. 9 is a device per this invention, wherein the device is molded so that an active insert can be placed within the molding.

FIG. 9 is a device as in FIG. 5 with the rectangular button molded thicker and containing a slot receptor for a separate capsule that contains an active substance.

Figure 10:
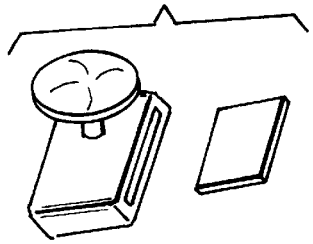
FIG. 10 shows a small square panel containing the active substance being placed inside the device.

FIG. 10 shows the active capsule about to be placed into the slot.

Figure 11:
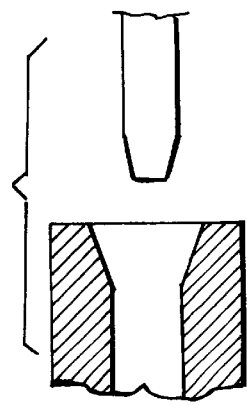
FIG. 11 is a side view that shows the active substance panel about to be placed into the device.

FIG. 11 shows a magnified view in cross-section of the active substance capsule about to be placed into the slot.

Figure 12:
FIG. 12 shows a device per this invention wherein a thin elastomeric sleeve is molded with a larger back panel.

FIG. 12 shows a device wherein a thin elastomeric sleeve is molded with a larger rectangular back panel.

Figure 13:
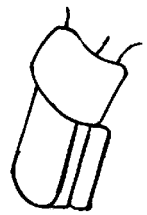
FIG. 13 shows how this sleeve is fitted onto a tooth.

FIG. 13 shows how the sleeve fits over a tooth.

Figure 14:
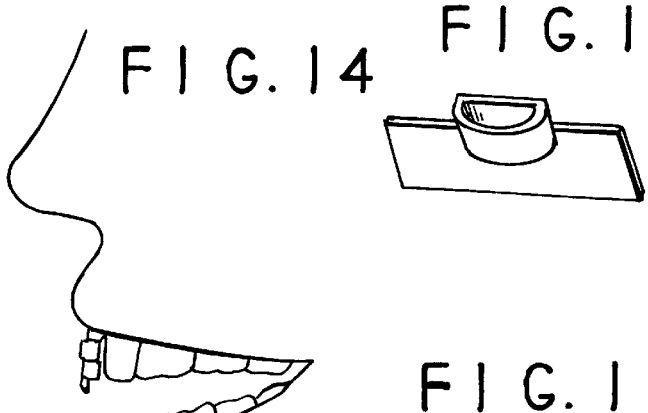
FIG. 14 shows how it is placed on the wearer's tooth.

FIG. 14. is a side view of the FIG. 12 device on the wearer's tooth.

Figure 15:
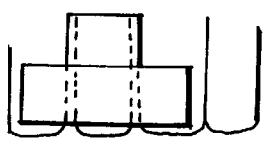
FIG. 15 is a view at the back side of the wearer's teeth indicating how the device is placed.

FIG. 15 is a view from the back side of the wearer's teeth indicating how the device is placed.

Figure 16:
FIGS. 16–18 are sketches of a device per my invention in which a separate disc or rectangular sheet of active ingredient is placed onto the stem of a device as in FIG. 1 before insertion in the manner described above.
Figure 17:
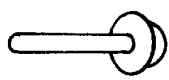

FIG. 16 is a disc containing active substance. It has a small hole in the center so that it can be placed onto the stem of a device as shown in FIG. 17.

Figure 18:
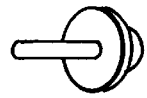

FIG. 18 shows the combination of the FIG. 16 active substance with the mushroom.

Figure 19:
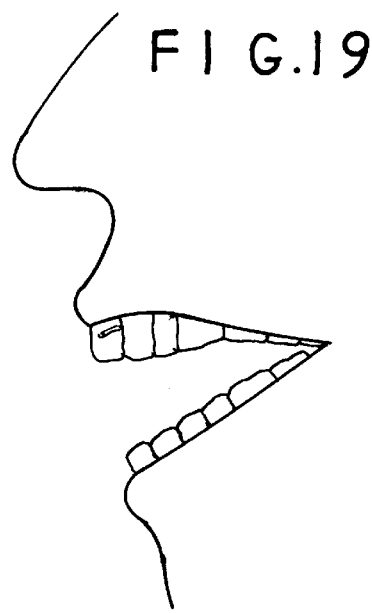
FIG. 19 shows the FIG. 18 combination placed into the mouth between two teeth.

FIG. 19 shows the FIG. 18 device placed in the wearer's mouth.

Figure 20:
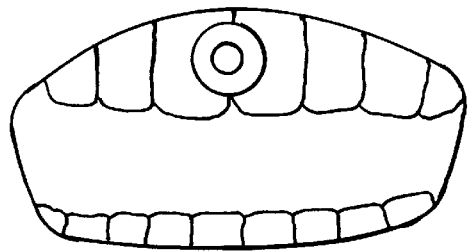
FIG. 20 shows the FIG. 18 combination as it might be viewed from inside the mouth.

FIG. 20 shows the device as it would be viewed from inside the mouth of the wearer.

Preferred dimensions of a separate active substance sheet or disc as shown in FIG. 16, is a sheet that is ½-inch×⅜-inch×0.060-inch thick with a 0.09-inch hole in the center. One of the advantages of this design is that it is a convenient method for administering two different active substances simultaneously, For example, the main mushroom head will contain an odorant such as peppermint oil while the sheet will have nicotine or a medication as the active substance.

Figure 21:
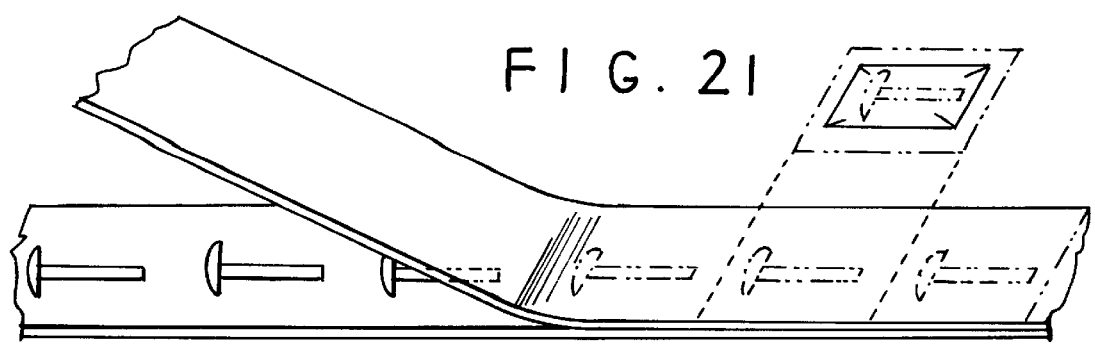
FIG. 21 shows a preferred method for packaging and shipment of the devices per this invention in a barrier film or foil package.

FIG. 21 shows individual units that are heat sealed between two strips of a barrier film or aluminum foil laminate.

Figure 22:
FIG. 22 shows a cross-section of an individual unit in the packaged pouch.

FIG. 22 shows a cross-section of an individual pouch containing one device. Alternatively, multiple units are packaged in a blister pack that is formed from barrier film or an aluminum foil laminate.

Although this invention has been described with a certain degree of particularity, it is to be understood that the present disclosure has been made only by way of illustration and that numerous changes in the details of the device design, matrix polymers and active substances may be resorted to without departing from the spirit and scope of this invention. These invented products will be suited for many diverse applications where it is desirable to have an unobtrusive device, which can quickly be inserted in the mouth and firmly placed in a fixed position between two teeth, and will slowly release an active substance.

I claim:

1. A device for slow release of substances into the oral cavity comprising:

a stretchable permeable elastomer polymer matrix containing an active ingredient which can permeate out when the device is inserted into the oral cavity, said matrix including a head extending laterally over adjacent teeth, and a stretchable stem of said elastomer polymer extending longitudinally from said head and having a stretchable thickness fitting and insertable between adjacent teeth, the thickness of said stem being decreased upon stretching and insertion between said teeth and returning to the original thickness upon relaxation for holding said device in position between the teeth.

2. The device of claim 1 wherein the head is in the shape of a mushroom positioned in the mouth behind the teeth.

3. The device as in claim 2 wherein the mushroom shaped head is approximately 0.25-inch in diameter and about 0.13-inch in thickness at the apex, with a stem that is about 0.3-inch in length and about 0.06-inch in diameter.

4. The device as in claim 1 wherein the stem has corrugations on the outer surface.

5. The device as in claim 1 wherein the device includes two heads in the shape of two small buttons connected with a short stem for holding said device between the teeth, the buttons ranging in size from $\frac{1}{16}$-inch in width to $\frac{3}{8}$-inch in width with one being larger than the other and the connecting stem being about 0.25-inch in length and about 0.060-inch in thickness, the smaller size button being placed at the front of the teeth so that the device is not readily apparent to any viewer.

6. The device as in claim 5 wherein the larger sized button is placed at the back of the teeth and has a thicker rectangular shape including a slot therein for placement of a capsule containing an active ingredient.

7. The device as in claim 2 including an elastomer sheet containing a second active ingredient, said sheet having a center hole engageable onto the stem adjacent to the head of the mushroom for placement within the mouth.

8. The device as in claim 1 wherein the polymer matrix used to manufacture the device is a room temperature vulcanizing (RTV) silicone rubber.

9. The device as in claim 1 wherein the polymer matrix that is used to manufacture the device is a thermoplastic elastomer that is injection moldable.

10. The device as in claim 1 wherein the active ingredient that is in the device and slowly permeates out is an odorant.

11. The device as in claim 1, wherein the active ingredient is nicotine.

12. The device as in claim 1 wherein the active ingredient that permeates out of the device is a medication.

13. The device of claim 1 including packaging means providing barrier films for long term storability of said elastomeric polymer matrix device.

* * * * *